United States Patent [19]

Wehner et al.

[11] 4,301,085

[45] Nov. 17, 1981

[54] PROCESS FOR THE PRODUCTION OF METHYL-ALKYL TIN DICHLORIDES

[75] Inventors: Wolfgang Wehner, Zwingenberg; Hans-Günter Köstler, Heppenheim/Bergstrasse, both of Fed. Rep. of Germany

[73] Assignee: Ciba-Geigy Corporation, Ardsley, N.Y.

[21] Appl. No.: 140,404

[22] Filed: Apr. 14, 1980

[30] Foreign Application Priority Data

Apr. 19, 1979 [CH] Switzerland .................. 3688/79

[51] Int. Cl.$^3$ .................................................. C07F 7/22
[52] U.S. Cl. .................................................. 260/429.7
[58] Field of Search .................................... 260/429.7

[56] References Cited

U.S. PATENT DOCUMENTS

| | | | |
|---|---|---|---|
| 3,471,539 | 10/1969 | Suzuki et al. | 260/429.7 |
| 3,475,472 | 10/1969 | Suzuki et al. | 260/429.7 |
| 3,475,473 | 10/1969 | Suzuki et al. | 260/429.7 |
| 3,519,665 | 7/1970 | Molt et al. | 260/429.7 |
| 3,857,868 | 12/1974 | Witman et al. | 260/429.7 |
| 3,862,198 | 1/1975 | Kugele et al. | 260/429.7 |
| 3,894,066 | 7/1975 | Buschhoff et al. | 260/429.7 |
| 3,901,824 | 8/1975 | Knezevic et al. | 260/429.7 X |
| 3,971,817 | 7/1976 | Jung et al. | 260/429.7 |
| 4,052,426 | 10/1977 | Wehner et al. | 260/429.7 |
| 4,052,427 | 10/1977 | Leistner et al. | 260/429.7 |

Primary Examiner—Helen M. S. Sneed
Attorney, Agent, or Firm—Luther A. R. Hall

[57] ABSTRACT

A process for the production of compounds of the formula I $$CH_3(R)SnCl_2 \qquad (I)$$

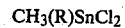

wherein R is $C_4$–$C_{20}$alkyl, which process comprises reacting dimethyl tin dichloride and R-Cl, wherein R has the above meaning, in the presence of a catalyst of the formula II $$R'(R''{}_3 M^{\oplus} X^{\ominus}) \qquad (II)$$

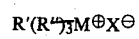

wherein R' is $C_1$–$C_{20}$alkyl which is unsubstituted or substituted by $C_1$–$C_4$alkoxy, or is $C_7$–$C_{20}$aralkyl, the aryl moiety of which can be substituted by halogen or $C_1$–$C_4$alkoxy, R" has the same meaning as assigned to R' or is phenyl which is unsubstituted or substituted by $C_1$–$C_4$alkyl, $C_1$–$C_4$alkoxy or halogen, $M^{\oplus}$ is a cation N, P or Sb, and X is an anion selected from the group consisting of chlorine, $SnCl_3$, $CH_3$-$SnCl_4$, $(CH_3)_2SnCl_3$, $SnCl_5$ or $SbCl_4$.

The compounds of the formula I are intermediates for obtaining stabilizers for halogen-containing thermoplastics.

12 Claims, No Drawings

PROCESS FOR THE PRODUCTION OF METHYL-ALKYL TIN DICHLORIDES

The present invention relates to a process for the production of methyl-alkyl tin dichlorides which are especially useful as intermediates for the manufacture of organo-tin stabilisers for halogen-containing thermoplastics.

Various syntheses for the production of dialkyl tin dichlorides are known. For example, U.S. Pat. No. 3,519,665 describes their production by direct alkylation in the presence of phosphonium iodide as catalyst. However, in order to obtain good yields it is necessary to recycle the by-products to the reaction space.

The production of methyl-alkyl tin dichlorides by transalkylation is known from U.S. Pat. No. 4,052,427. The reaction

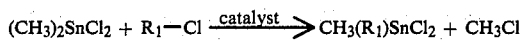

wherein $R_1$ is $C_2$–$C_{20}$ alkyl, proceeds only in the presence of the phosphonium iodide catalyst referred to above.

The use of iodine-containing catalysts has the disadvantage that it results in discolouration of the final product, which in turn is disadvantageous for the later use of this latter as starting material for the manufacture of the stabiliser. The object has therefore been to obtain long-chain alkyl tin halides which do not contain iodine.

The production of dimethyl tin dichlorides by direct alkylation, i.e. from tin and methyl chloride in the presence of phosphonium chloride as catalyst, is described in U.S. Pat. No. 3,901,824. As the reaction results in a good yield of virtually colourless product, it was obvious to prepare long chain alkyl tin halides also in this manner. However, experiments have shown that the use of phosphonium chloride as catalyst leads only to exceedingly poor results. The conclusion to be drawn was that phosphonium chloride is unsuitable as catalyst for obtaining alkyl tin halides, i.e. even by the method of transalkylation.

Surprisingly, it has now been found that colourless long-chain methyl-alkyl tin halides additionally containing alkyl tin trichlorides are obtained in good yield by a simple synthesis using phosphonium chloride as transalkylation catalyst.

Accordingly, the present invention provides a process for the production of compounds of the formula I $$CH_3(R)SnCl_2 \quad (I)$$

wherein R is $C_4$–$C_{20}$alkyl, which process comprises reacting dimethyl tin chlorides and R-Cl, wherein R has the above meaning, in the presence of a catalyst of the formula II

wherein R' is $C_1$–$C_{20}$alkyl which is unsubstituted or substituted by $C_1$–$C_4$alkoxy, or is $C_7$–$C_{20}$aralkyl, the aryl moiety of which can be substituted by halogen or $C_1$–$C_4$ alkoxy, R" can be identical or different radicals selected from the group R' or is phenyl which is unsubstituted or substituted by $C_1$–$C_4$alkyl, $C_1$–$C_4$alkoxy or halogen, M⊕ is a cation N, P or Sb, and X is an anion selected from the group consisting of chlorine, $SnCl_3$, $CH_3$—$SnCl_4$, $(CH_3)_2SnCl_3$, $SnCl_5$ or $SbCl_4$.

R as $C_4$–$C_{20}$alkyl is e.g. n-butyl, t-butyl, n-amyl, iso-amyl, tert-amyl, n-hexyl, 2-ethylhexyl, n-octyl, n-decyl, n-dodecyl, 11-methyldodecyl, n-tetradecyl, n-hexadecyl, 16-methylheptadecyl and 2-eicosyl. It is preferred that R is a straight chain alkyl radical containing 4 to 12 carbon atoms, such as n-butyl, n-decyl, and especially n-dodecyl.

R' as $C_1$–$C_{20}$alkyl which can be substituted by $C_1$–$C_4$alkoxy is e.g. methyl, ethyl, n-propyl, isopropyl, n-butyl, tert-amyl, n-octyl, n-dodecyl, 11-methyldodecyl, n-tetradecyl, 16-methylheptadecyl, nonadecyl, 2-ethoxyethyl, 4-ethoxybutyl. It is preferred that R' is a straight-chain $C_1$–$C_4$alkyl radical, such as methyl, ethyl, n-propyl or especially n-butyl.

R' as $C_7$–$C_{20}$aralkyl is e.g. benzyl or 1-phenylethyl, and if the aryl moiety is substituted by halogen or $C_1$–$C_4$alkoxy can be e.g. 2-methoxybenzyl, 2-methoxyphenylethyl, 3-chlorobenzyl. The preferred identity of R' is benzyl.

R" can have the same meaning as R' or can be phenyl, 3-methoxy-phenyl, tolyl, xylyl or 4-chlorophenyl. It is preferred that R" is phenyl, benzyl or n-butyl. The most preferred identity of R" is n-butyl.

M⊖ is N, P and Sb, preferably P. X is a chlorine-containing anion, e.g. chlorine, $SnCl_3$, $CH_3$—$SnCl_4$, $(CH_3)_2Sn_nCl_3$, $SnCl_5$ or $SbCl_4$. It is preferred that X is $SnCl_5$.

The most preferred catalyst is tributylmethylphosphonium pentachlorostannate (IV).

Examples of compounds of formula I are:
methyl-n-butyl tin dichloride
methyl-n-hexyl tin dichloride
methyl-n-decyl tin dichloride
methyl-n-dodecyl tin dichloride
methyl-iso-tridecyl tin dichloride
methyl-n-tetradecyl tin dichloride.

In the process of the invention, the molar ratio of dimethyl tin dichloride to R—Cl is usually about 1:1. It is preferred to use a small excess of R—Cl.

The reaction can be carried out in the temperature range from 160° to 240° C., with the preferred range being from 180° to 200° C. The reaction medium can also contain customary inert solvents, e.g. aliphatic and aromatic hydrocarbons, ethers, esters, cyclic carbonates, sulfoxides or sulfolanes. However, the preferred solvents are $(CH_3)_2SnCl_2$ or R—Cl.

The catalyst can be employed in amounts of 5 to 50 mol. %, based on $(CH_3)_2SnCl_2$. The preferred amount is 10 to 30 mol. %.

The starting dimethyl tin dichloride and the onium chloride catalyst can be obtained in known manner as described in U.S. Pat. No. 3,901,824. The compounds R—Cl are known or they can be obtained by methods commonly known in the art.

The compounds of the formula I are important intermediates for the manufacture of organo-tin stabilisers which are used for halogen-containing thermoplastics, such as PVC. Such manufacture includes the reaction of organic fatty acids containing 6 to 18 carbon atoms with alkylthiols, mercapto esters or alcohols, as described e.g. in Canadian patent specification No. 595,138.

The compounds of the formula I produced by the process of this invention is obtained as a mixture with R—$SnCl_3$ and $CH_3SnCl_3$, wherein R is $C_4$–$C_{20}$alkyl.

The reaction mixture can be used direct for further processing to give a stabiliser. The content of alkyl tin trichloride, which is only obtainable with difficulty by conventional methods, acts as synergist in the stabiliser.

The process of the present invention results in surprisingly good yields. A great advantage of the onium catalysts employed is that they do not lead to any discolouration of the products. Aside from this advantage, they are also cheaper than iodine-containing catalysts. The high yield is obtained without recycling the by-products to the reaction space. A further advantage compared with the process using phosphonium iodide catalysts is that alkyl tin trichloride is obtained. This compounds acts as synergist in a stabiliser produced direct from the reaction mixture.

The invention is illustrated in more detail by the following Example, in which percentages are by weight.

EXAMPLE

A three-necked flask equipped with stirrer and reflux cooler is charged at 180° C. with 0.2 mole of $(CH_3)_2SnCl_2$ and 0.05 mole of catalyst. Then 0.4 mole of lauryl chloride is slowly added over the course of 4 hours while gradually raising the temperature to 200° C. Stirring is then continued for a further 2 hours at 200° C.

When the elimination of methyl chloride is complete, the resultant mixture has the following composition (analysis by gas chromatography):

| Catalyst | [CH$_3$(CH$_2$)$_3$]$_3$—P$^{\oplus}$CH$_3$ J$^{\ominus}$ (comparison) | [CH$_3$(CH$_2$)$_3$]$_3$—P$^{\oplus}$CH$_3$ SnCl$_5$$^{\ominus}$ |
|---|---|---|
| (CH$_3$)$_2$SnCl$_2$-reaction in % | 87.1 | 93.7 |
| Sn-distribution in % (CH$_3$)$_2$SnCl$_2$ | 12.9 | 6.3 |
| CH$_3$[CH$_3$(CH$_2$)$_{11}$]—SnCl$_2$ | 81.6 | 63.5 |
| CH$_3$SnCl$_3$ | 5.5 | 12.1 |
| CH$_3$(CH$_2$)$_{11}$SnCl$_3$ | — | 18.1 |

$CH_3[CH_3(CH_2)_{11}-SnCl_2$ can be separated as main component by distillation. Melting point: 43°–45° C.

What is claimed is:

1. A process for the production of a compound of the formula I $$CH_3(R)SnCl_2 \qquad (I)$$

wherein R is $C_4$–$C_{20}$alkyl, which process comprises reacting dimethyl tin dichloride and R—Cl, wherein R has the above meaning, in the presence of a catalyst of the formula II $$R'(R'')_3M^{\oplus}X^{\ominus} \qquad (II)$$

wherein R' is $C_1$–$C_{20}$alkyl which is unsubstituted or substituted by $C_1$–$C_4$alkoxy, or is $C_7$–$C_{20}$aralkyl, the aryl moiety of which can be substituted by halogen or $C_1$–$C_4$alkoxy, R'' can be identical or different radicals selected from the group R' or is phenyl which is unsubstituted or substituted by $C_1$–$C_4$alkyl, $C_1$–$C_4$alkoxy or halogen, $M^{\oplus}$ is a cation N, P or Sb, and X is an anion selected from the group consisting of $CH_3$—$SnCl_4$, $(CH_3)_2SnCl_3$, $SnCl_5$ or $SbCl_4$.

2. A process according to claim 1 for the production of a compound of the formula I in admixture with R—SnCl$_3$ and CH$_3$SnCl$_3$, wherein R is as defined in claim 1.

3. A process according to claim 1, wherein R is straight chain $C_4$–$C_{12}$alkyl.

4. A process according to claim 1, wherein R' and R'' are $C_1$–$C_{20}$alkyl.

5. A process according to claim 1, wherein R' and R'' are straight chain $C_1$–$C_4$alkyl.

6. A process according to claim 1, wherein $M^{\oplus}$ is P.

7. A process according to claim 1 for the production of methyl-n-dodecyl tin dichloride.

8. A process according to claim 1, wherein the catalyst is tributylmethylphosphonium pentachlorostannate (IV).

9. A process according to claim 1, wherein the reaction is carried out in the temperature range from 160° to 240° C.

10. A process according to claim 1, wherein the reaction is carried out in the presence of an inert solvent.

11. A process according to claim 10, wherein the solvent is $(CH_3)_2SnCl_2$ or R—Cl, wherein R is as defined in claim 1.

12. A process according to claim 1, wherein the catalyst is used in an amount from 5 to 50 mol. %, based on the dimethyl tin dichloride employed.

* * * * *